United States Patent
Schramm et al.

(10) Patent No.: US 6,793,149 B2
(45) Date of Patent: Sep. 21, 2004

(54) METHOD AND APPARATUS FOR EVAPORATING MULTI-COMPONENT LIQUIDS

(75) Inventors: Heather R. Schramm, Whitewater, WI (US); Edward J. Martens, III, Racine, WI (US); Susan M. Clausen, Zion, IL (US); Padma P. Varanasi, Racine, WI (US); Jesse Ben Crandall, Drummond, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 326 days.

(21) Appl. No.: 10/066,814

(22) Filed: Feb. 4, 2002

(65) Prior Publication Data

US 2003/0146292 A1 Aug. 7, 2003

(51) Int. Cl.[7] .................................................. B05B 3/04
(52) U.S. Cl. .............................. 239/102.1; 239/102.2; 239/4; 73/53.01
(58) Field of Search ..................... 239/4, 102.1, 102.2, 239/338; 73/53.01, 64.48, 64.52, 64.53

(56) References Cited

U.S. PATENT DOCUMENTS

| | | |
|---|---|---|
| 2,607,571 A | 8/1952 | Hession, Jr. |
| 4,085,893 A | 4/1978 | Durley, III .................. 239/102 |
| 5,011,632 A | 4/1991 | Yano et al. |
| 5,173,274 A | 12/1992 | Owen .......................... 422/306 |
| 5,601,235 A | 2/1997 | Booker et al. ................. 239/4 |
| 5,894,001 A | 4/1999 | Hitzler et al. ................. 261/92 |
| 6,296,196 B1 | 10/2001 | Denen et al. .................. 239/4 |

FOREIGN PATENT DOCUMENTS

| | | |
|---|---|---|
| DE | 3 441 317 | 8/1986 |
| EP | 0897755 A2 | 2/1999 |
| EP | 0 897 755 | 2/1999 |
| WO | 00/58709 | 10/2000 |

OTHER PUBLICATIONS

D.Y. Kwok, et al., "Axisymmetric Drop Shape Analysis as a Film Balance", Colloids and Surfaces A:Physicochemical and Engineering Aspects 88 (1994) 51–58.

*Primary Examiner*—David A. Scherbel
*Assistant Examiner*—Thach H. Bui
(74) *Attorney, Agent, or Firm*—Fitzpatrick, Cella, Harper & Scinto (57) ABSTRACT

An atomizer 10 atomizes a multi-component liquid from a reservoir 20 into a cloud 14 comprising small droplets 38 which are ejected into the atmosphere to a certain height and allowed to fall toward a surface 12. Essentially complete evaporation is assured by maintaining the size of the droplets, the liquid's component vapor pressures and the height through which the droplets fall according to a predetermined relationship. Also, the suitability of a liquid for evaporation in a vibrating plate atomizer is determined by measuring the rate of size decrease and the surface tension of a pendant drop of the liquid after a predetermined amount of the liquid has evaporated from the drop.

42 Claims, 6 Drawing Sheets

METHOD AND APPARATUS FOR EVAPORATING MULTI-COMPONENT LIQUIDS

BACKGROUND OF THE INVENTION

1. Field of the Invention

This invention relates to the dispersal of a multi-component liquids, such as insecticides and fragrance solutions, by ejecting a cloud or mist of small droplets of the liquid from a vibrating atomization plate into the atmosphere and evaporating the liquid components from the droplets as they fall back through the atmosphere.

2. Description of the Related Art

It is well known to disperse fragrances and insecticides into the atmosphere by using a vibrating atomization plate to form a mist or cloud of small droplets of a solution containing the fragrance or insecticide and to eject the mist or cloud into the atmosphere in the form of minute liquid droplets. As the mist or cloud settles, the fragrance or insecticide evaporates from the droplets. Examples of devices for doing this are shown in U.S. Pat. No. 4,085,893, U.S. Pat. No. 5,173,274, U.S. Pat. No. 5,601,235 and U.S. Pat. No. 5,894,001. In general these devices supply the liquid fragrance or insecticide to a vibrating atomization plate which, due to its vibrations, breaks up the liquid into fine droplets and ejects them upwardly in the form of a mist or a cloud. As the droplets fall back down, the fragrance or insecticide evaporates from the droplets and disperses into the atmosphere.

A problem occurs in the operation of these known devices in that there is no means to be sure that all of the liquid which is ejected will evaporate before the droplets fall back onto surrounding surfaces. As a result, an unsightly and often destructive liquid residue of unevaporated liquid builds up on these surfaces. This problem is particularly difficult where the liquid to be ejected is a fragrance or an insecticide. This is because fragrance and insecticide compositions are generally quite complex; and there has been no way to know in advance that a particular composition will fully evaporate when subjected to atomization in a vibrating plate atomizer.

SUMMARY OF THE INVENTION

The present invention substantially overcomes the problem of undesired buildup of unevaporated liquid which has been ejected from a vibrating plate atomizer as a mist or cloud into the atmosphere. The invention is based on the discovery that when liquid compositions are broken up into small droplets and ejected into the atmosphere above a surrounding surface, such as a table top, for example, the ability of those droplets to become fully evaporated before they fall back onto the surrounding surface, does not depend on the vapor pressure of the liquid composition itself. Instead the ability of the droplets to evaporate depends upon the vapor pressures of the individual components of the liquid composition. The invention is also based on the discovery that the vapor pressure of the lowest vapor pressure component of the liquid composition must be such that this component will evaporate before the liquid droplet which contains the component reaches the surrounding surface.

According to one aspect of the invention, there is provided a novel method of evaporating a multi-component liquid solution, particularly, a multi-component liquid fragrance or a multi-component liquid insecticide in a manner such that the amount of liquid deposited on adjacent surfaces is minimized. This novel method involves the steps of using a vibrating plate atomizer to form a mist or cloud of small liquid droplets of the solution, ejecting the mist or cloud into the atmosphere and allowing the droplets to fall back toward an adjacent surface. The liquid solution comprises a plurality of components having respective vapor pressures; and the component having the lowest vapor pressure is related to those droplets having the larger diameters such that $$1.2 \times 10^{12} \times D_p^4 / [H \times P_v] \leq 1$$

where $D_p$ is the diameter, in centimeters, of the large diameter droplets, H is substantially the height, in centimeters, to which the large diameter droplets are ejected above the adjacent surface, and $P_v$ is the vapor pressure, in millimeters of Hg, of those components having the lowest vapor pressure. In this manner, the amount of unevaporated liquid that falls back upon the adjacent surface is minimized. In more specific aspects, the values $D_p$, H and $P_v$ are chosen in conjunction with the effects of the liquid on the adjacent surface such that any unevaporated liquid that does fall back onto the adjacent surface will be in an amount insufficient to cause an adverse effect on the surface.

According to another aspect of the invention, there is provided a novel apparatus for evaporating a multi-component solution, particularly a multi-component liquid fragrance or a multi-component liquid insecticide. This novel apparatus comprises a liquid reservoir containing a multi-component liquid, a liquid delivery system and a vibrating plate atomizer. The liquid delivery system is arranged to convey liquid from the reservoir to the atomizer. The atomizer in turn is constructed to form a mist or cloud of small liquid droplets and to eject these droplets into the atmosphere. The droplets have diameters within a predetermined range, and they are ejected to predetermined heights above an adjacent surface. As the droplets fall back toward the surface they evaporate to an extent that no or only a negligible amount of liquid falls upon the adjacent surface. The liquid comprises a plurality of components having respective vapor pressures; and the component having the lowest vapor pressure is related to those droplets having the larger diameters such that $$1.2 \times 10^{12} \times D_p^4 / [H \times P_v] \leq 1$$

where $D_p$ is the diameter, in centimeters, of the larger diameter droplets, H is the height in centimeters, to which the larger diameter droplets are ejected and $P_v$ is the vapor pressure, in millimeters of Hg, of those liquid components having the lowest vapor pressure. In this manner the amount of unevaporated liquid that falls back upon the adjacent surface is minimized. In more specific aspects, the values $D_p$, H and $P_v$ are chosen in conjunction with the effects of the liquid on the adjacent surface such that any unevaporated liquid that does fall back onto the adjacent surface will be in an amount insufficient to cause an adverse effect on the surface.

In a still further aspect, the present invention is based on the discovery that the evaporation of an atomized droplet can be predicted by the evaporation rate of a pendant drop of the liquid by Axisymmetric Drop Shape Analysis (ADSA). In this technique, a drop of known size is formed at the end of a capillary. Then, while the drop is exposed to the atmosphere, measurements are taken of the rate at which its size decreases. If the rate at which the size of the pendant drop decreases is greater than a given threshold, then the liquid is suitable for use in an atomizer. That is, evaporation of an atomized droplet from the atomizer will be sufficiently complete before the droplet can reach the adjacent surface. The given threshold is chosen such that for the diameter of the droplets comprising the mist or cloud, and the height to which they are ejected above the adjacent surface, substantially all of the liquid will evaporate before the droplets fall back onto the adjacent surface.

In a more specific aspect, the threshold is established by measuring the rate at which the size of a pendant drop of the liquid decreases. This corresponds to the rate of evaporation of liquid from the pendant drop. In the case of a multi-component liquid fragrance or a multi-component liquid insecticide where the pendant drop of the liquid is about 6 microliters, the evaporation rate should be measured when approximately 70% of the volume of the drop has evaporated.

Other specific aspects of the invention involve novel apparatus for ascertaining the rate at which a test pendant drop of a liquid decreases in size, and methods and apparatus for ascertaining evaporability based on measurements of surface tension of a droplet of the liquid.

DETAILED DESCRIPTION OF THE PREFERRED EMBODIMENTS

Figure 1:
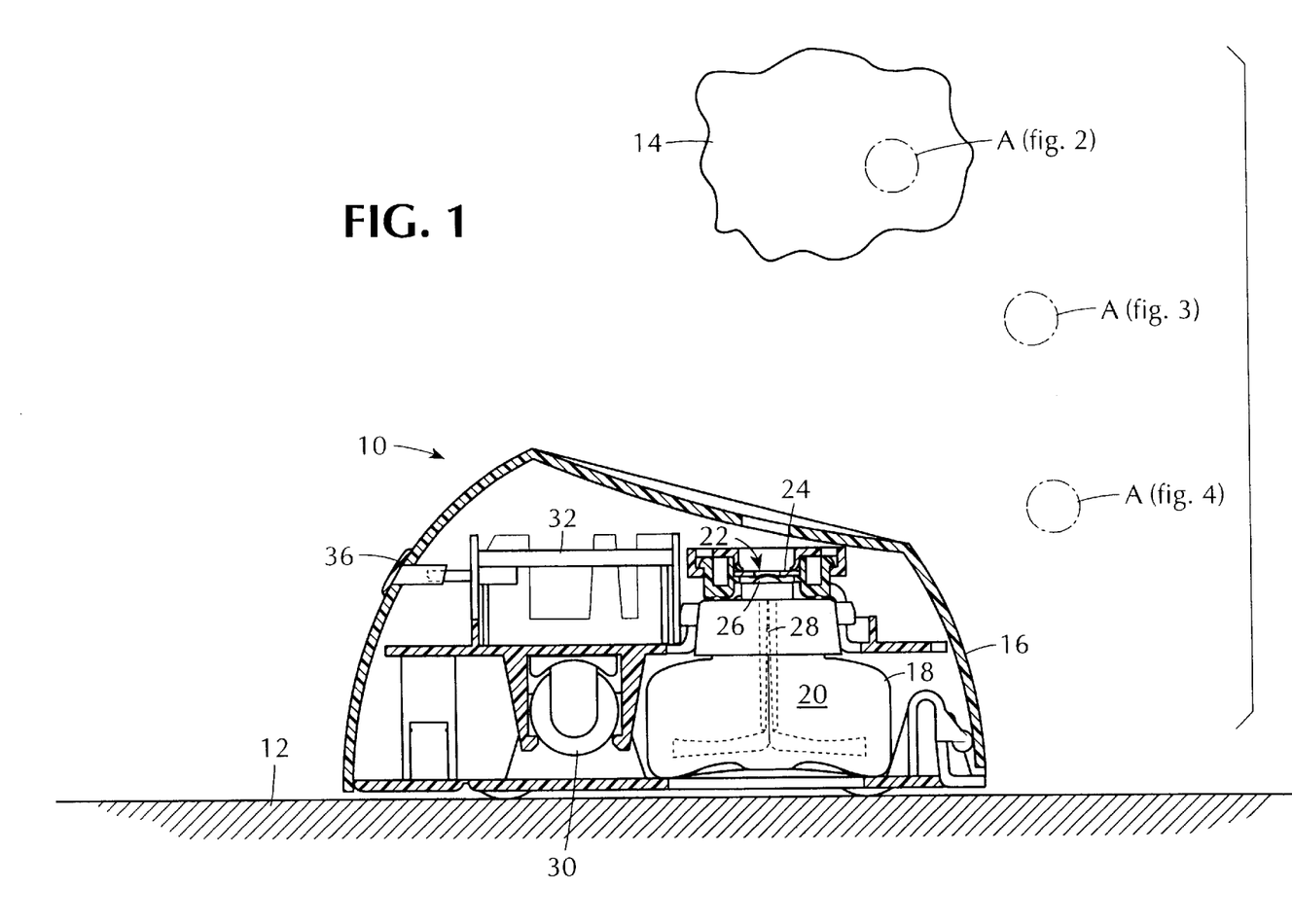
FIG. 1 is a side elevational section view of an atomizing device resting on a surface and ejecting small liquid droplets into the atmosphere.

As shown in FIG. 1, a piezoelectric liquid atomizer device 10 rests upon an adjacent surface 12, which may be a table top; and ejects a cloud 14 of small liquid droplets in the form of a fine mist into the atmosphere to a height, for example, of about 5 to 20 centimeters above the surface 12. The droplets then fall back toward the top of the atomizer device and toward the surface 12 itself As the droplets fall, they evaporate so that no liquid or only a very small amount of the liquid in the ejected droplets actually contacts the top of the atomizer device 10 or the surface 12.

The atomizer device 10 comprises an outer housing 16 in which a reservoir 18 is mounted. The reservoir 18 contains a liquid 20 to be ejected into the atmosphere. An atomizer assembly 22 is mounted in the housing 16 just above the reservoir 18. The atomizer assembly 22 comprises an annularly shaped piezoelectric actuator 24 and a circularly shaped orifice plate 26. The orifice plate extends across a center opening of the actuator 24 and is fixed to the actuator around this center opening, for example by soldering. When alternating electrical fields are applied across upper and lower surfaces of the actuator 24 the actuator expands and contracts in radial directions. These movements are communicated to the orifice plate 26 and cause it to flex so that its center region vibrates rapidly up and down. Liquid 20 from the reservoir 18 is supplied to the underside of the vibrating orifice plate 26 by a liquid delivery system 28, such as a wick. The center region of the orifice plate 26 is formed with a plurality of small orifices which extend from its lower surface to its upper surface. The exit diameters of these orifices is preferably in the range of 3–6 microns. As the plate 26 vibrates up and down it pumps the liquid 20 through the orifices and ejects the liquid in the form of the cloud 14 of small droplets into the atmosphere.

The outer housing 16 also contains a battery 30 which supplies electrical power to an electrical circuit formed on a printed circuit board 32 within the housing. The electrical circuit converts electrical power from the battery 30 into alternating electrical voltages which are applied via a pair of voltage supply lines (not shown) to the upper and lower surfaces of the actuator 24. These alternating electrical voltages, which have a frequency in the range of 130 Khz to 160 Khz, cause the orifice plate 26 to vibrate at frequencies and amplitudes sufficient to produce the cloud 14 and eject it into the atmosphere to a height, for example, in the range of 5 to 20 centimeters above the surface 12. The size of the cloud 14 depends on the duration of vibration of the orifice plate 26. This duration, which in the illustrative embodiment, is 11 milliseconds, is not part of the invention.

A switch 36 is provided on the housing 16 and is coupled to the electrical circuit on the printed circuit board 32. This switch can be set to provide adjustable time periods between the production of successive clouds 14. The period between the production of successive clouds 14 may be adjusted by means of the switch 36 between about 9 and about 40 seconds. The range of adjustment may be increased or decreased according to the desired overall rate at which the liquid is to be dispersed into the atmosphere, provided that it allows sufficient time for each cloud 14 to evaporate before the next cloud is formed; and it allows for formation of clouds over extended periods of time, for example several days. In some cases it may be desired to form a continuous mist or cloud. For this purpose, the switch 36 is provided with a setting that will produce continuous vibration of the orifice plate 26 and continuous atomization of the liquid 20.

The internal construction and operation of the piezoelectric atomizer device 10 itself does not form part of this invention and therefore it will not be described in further detail herein. A piezoelectric atomizer device which is suitable for use in the present invention is shown and described in U.S. application Ser. No. 09/519,560, filed on Mar. 6, 2000 (now U.S. Pat. No. 6,296,196 B1, issued Oct. 2, 2001); and the disclosure of that application is incorporated herein by reference.

Figure 2:
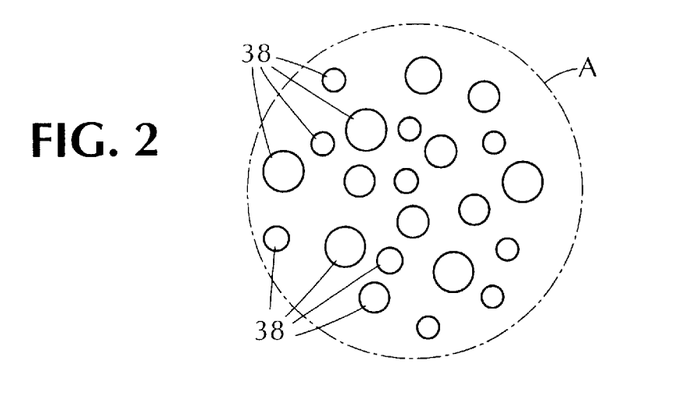
FIGS. 2–4 are enlarged diagrammatic views illustrating size decrease in ejected droplets as they fall through the atmosphere.
Figure 3:
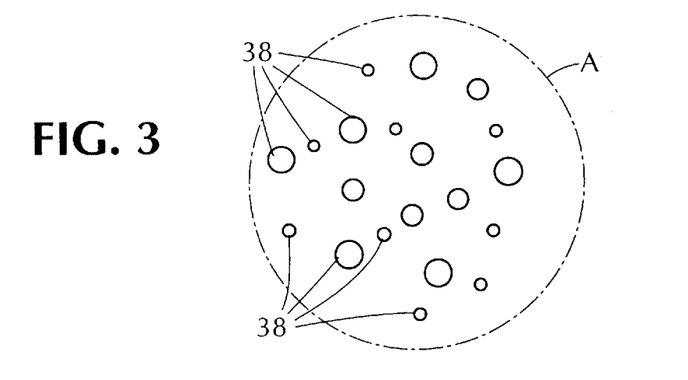
Figure 4:
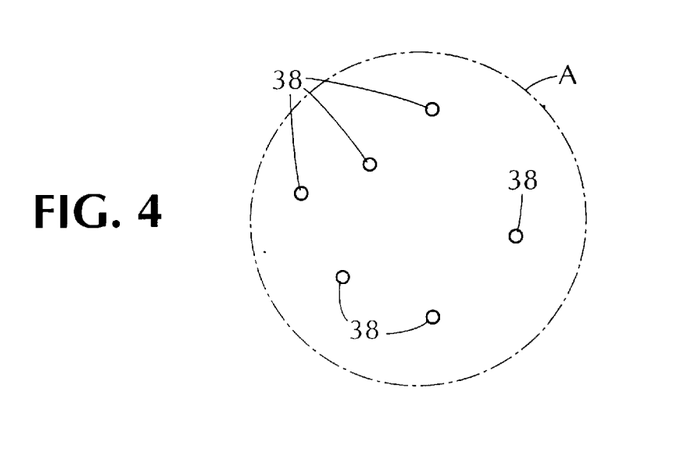

FIG. 2 is an enlarged stylized representation of droplets 38 contained within a region A of the cloud 14. As can be seen, the droplets 38 vary in diameter and they are ejected to various heights within the cloud 14. It is preferred to have the droplets 38 as small as possible because small droplets evaporate more readily than larger diameter droplets. However, a limiting factor in the formation of small droplets is the minimum diameter of the orifices in the orifice plate 26. In general, this minimum diameter is about 3 microns because of manufacturing limitations. The droplets 38 themselves will vary in diameter from about 1 to about 50 microns, with the average droplet size being 5 to 6 microns. There may be some smaller and some larger diameter droplets but these should be no more than a negligible amount of the total liquid volume of the cloud 14. For example, in the case of most air fresheners, no more than 10% of the total liquid volume of the cloud 14 should have a diameters greater than 10 microns. As mentioned above, the droplets 38 which form the cloud 14 are ejected to heights between 8 and 15 centimeters above the surface 12. FIGS. 3 and 4 show the region A at different elevations as the cloud 14 falls toward the surface 12. FIGS. 3 and 4 are meant to show that the droplets 38 each become smaller as liquid evaporates from their outer surfaces during their fall back toward the surface 12.

A single liquid droplet, comprising a single chemical component, when falling through the atmosphere will evaporate according to the following formula:

$$P_v > [D_p^4 \times \Delta\rho \times g \times R \times T \times \rho_D]/[2.639 \times \mu \times H \times M \times D_{AB}]$$

where:

$P_v$=vapor pressure of the component (mm of Hg);

$D_p$=diameter of the particle (cm);

$\Delta\rho$=density difference between liquid droplet and the ambient air (g/cm$^3$);

g=gravitational constant (g/sec$^2$);

R=universal gas constant (atm cc/g mole Kelvin);

T=absolute temperature (Kelvin);

$\rho_D$=density of the liquid droplet (g/cm$^3$);

$\mu$=viscosity of the ambient air (poise);

H=height from which the liquid droplet falls to the surrounding surface (cm);

M=molecular weight of air (g mole); and $D_{AB}$=diffusion coefficient of liquid droplet in air (cm$^2$/sec).

While each of these factors affect the evaporation of the liquid droplet to some degree, only three of them, namely vapor pressure of the single component liquid droplet ($P_v$); diameter of the liquid droplet ($D_p$); and height from which the droplet falls (H) have a sufficiently greater effect on evaporation that the other variables may be assumed constant. It should be noted that temperature does have a significant effect on evaporation; however, in the environment in which a liquid fragrance or an insecticide is to be evaporated, namely, in a room or other enclosed space where the temperature is in the range of normal living conditions, e.g. 23 to 27° C., the effects of temperature can be accommodated. Thus, for a droplet 38 which falls from a height in the range of about 5 to 20 centimeters above the surface 12, the following relationship must be maintained between the initial diameter of the droplet and its vapor pressure:

$$D_p^4 \leq (H \times P_v)/(1.2 \times 10^{12}).$$

Where different heights of fall are to be considered, the following relationship must be maintained:

$$D_p^4 \leq ((H) \times (P_v))/(1.2 \times 10^{12}).$$

The foregoing applies for a droplet which contains a single liquid component. However fragrances and insecticide formulations are generally composed of several different liquid components in mixture or solution; and, in the case of fragrances, the number of such components may be between one hundred and two hundred.

The applicants have discovered that the above formulae, which relate droplet diameter and vapor pressure, do not hold for a multi-component liquid. That is, if the overall vapor pressure of a multi-component liquid is used in the foregoing formulae, droplets of that multi-component liquid will not evaporate completely before they fall from a height of 5 to 20 centimeters. The applicants have discovered that in order to calculate the evaporation of droplets of a multi-component liquid, the vapor pressure of the individual components of the liquid must be considered and not the overall vapor pressure of the liquid. Instead, the calculation of evaporation must be based upon the vapor pressure of the lowest vapor pressure component of the liquid composition.

When a liquid mixture from a reservoir is formed into droplets, each individual droplet, no matter how small, comprises each of the components of the liquid mixture in the same percentage that exists in the reservoir. Further, when liquid is evaporated from a liquid droplet, each component of the liquid evaporates at a rate proportional to its own individual vapor pressure. Therefore the highest vapor pressure component will evaporate preferentially while the components having successively lower vapor pressures will evaporate more slowly. The entire droplet will not evaporate until the component having the lowest vapor pressure evaporates. By using the above formulas, (which relate droplet size to vapor pressure and/or height), the amount of atomized liquid which falls back on the surface 12 is minimized.

It should be understood that when droplets are formed in an atomizing device, the droplets will be formed in a range of diameters and will be ejected to a range of heights above the surface toward which they fall. It should also be understood that the vapor pressures of the components of the liquid being atomized may have a wide range. Because of this, some of the droplets may not entirely evaporate before they fall onto the surface. This may be acceptable, provided the amount of non-evaporated liquid that falls on the surface is minimal. What is acceptable will depend on the amount and nature of the non-evaporated liquid that falls onto the surface and on the nature of the surface, e.g. the chemical effect of the non-evaporated portion of the liquid on that surface.

Where liquid compositions, such as fragrances or insecticides, comprise large numbers of components, it is often not practical to ascertain the vapor pressures of each of the individual components in order to determine the evaporation characteristics of atomized droplets of the liquid. Often, the liquid components themselves are not known because the fragrance or insecticide is maintained by the supplier as a trade secret.

Figure 5:
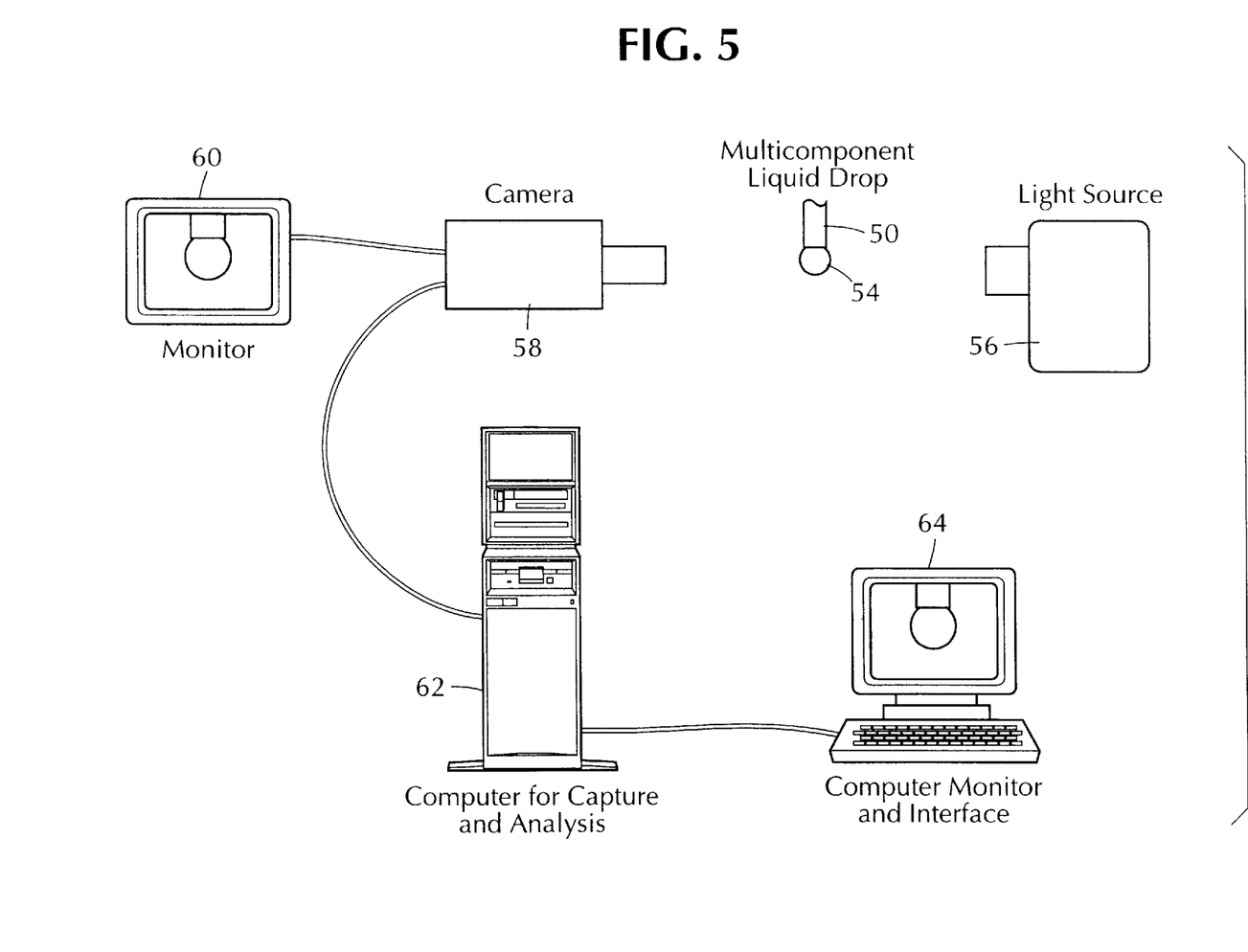
FIG. 5 is a schematic of a pendant drop size measurement system used in one aspect of the invention.

The arrangement shown in FIG. 5 enables one to predict whether a liquid will be suitable for use in an atomizer. As shown in FIG. 5, there is provided a droplet forming syringe 50 which forms a pendant test drop 54 of a liquid 54 being considered for use in an atomizer such as the atomizer 10 of FIG. 1. The size of the pendant test drop 54 in this embodiment is about 6 microliters, although the exact size of the pendant drop is not critical to this invention. Liquid is allowed to evaporate from the pendant test drop 54 while it is suspended from the syringe 50 under conditions which are similar to those which would be encountered by a mist or cloud of atomized droplets of the liquid when they fall back to a surface after being ejected into the atmosphere. As liquid evaporates from the drop 54, its size decreases and its profile changes. By observing the rate at which the droplet size decreases, the differential evaporation rate of the material can be calculated. Also, by observing the profile changes of the drop 54, its surface tension, which also affects atomization, can be ascertained.

As can be seen in FIG. 5, the test drop 54 is positioned between a light source 56 and a camera 58, and thus modifies the light from the light source which is incident on the camera. The camera 58 responds to the modified light to generate droplet size and profile images in the form of electrical signals. A monitor 60 is connected to receive image signals from the camera 58 to enable one to be sure that the droplet size and profile is being properly recorded by the camera 58. In addition, the electrical image signals from the camera 58 are supplied to a computer 62. The computer 62 is programmed to record the size of the drop 54, and of its profile, at successive times so that the rates of change of the drop size and profile can be ascertained. The computer 62 is also connected to a monitor 64 which produces images showing the rates of change of droplet size and profile. The camera 58 and the computer 62 serve as a sensor which is constructed and arranged to sense a rate of decrease in the size of the pendant test droplet 54 during evaporation of liquids therefrom. Also, the monitor and interface 64 serves as an indication producing device which is connected to the sensor (camera 58) and computer 62 to produce a signal which represents suitability for atomization of the liquid when the sensor indicates that the rate of decrease is greater than a predetermined rate.

In operation of the apparatus of FIG. 5, a pendant test drop 54 of a liquid under consideration is produced by and is suspended from the syringe 50. The test droplet is allowed to evaporate while the camera 58 generates images corresponding to the droplet size and profile. It has been found preferable, in the case of a multi-component liquid fragrance or a multi-component liquid insecticide, to initially form a 6 microliter pendant drop and to observe its rate of size decrease and its rate of profile change after about 70% of the pendant drop has evaporated. At this point the higher vapor pressure components of the drop have been removed through evaporation; and the components which are slowest to evaporate are available for analysis. This analysis is continued until about 80% of the initial drop volume has evaporated.

The evaporation characteristics of atomized droplets of the liquid correspond, to a great extent, to the rate at which the pendant test drop 54 decreases in size as liquid components evaporate therefrom. The atomization characteristics of atomized droplets of the liquid also correspond, to a great extent, on the surface tension of the drop 54. It has been found that a multi-component liquid fragrance or a multi-component liquid insecticide which is atomized in a vibrating plate atomizer which forms droplets up to 50 microns and ejects them to a height of at least 8 centimeters above a surface toward which they fall, will essentially completely evaporate if a 6 microliter pendant drop of the liquid, after being about 70% evaporated, shows an evaporation rate of greater than about $1.0 \times 10^{-8}$ cubic meters per square centimeter per second when the surface tension is below 35 dynes per centimeter.

The rate of size decrease of the pendant test drop 54 can be ascertained by observing the rate of decrease of its diameter during evaporation of liquid components therefrom. Also, the surface tension of the pendant test drop 54 can be ascertained by observing changes in its profile during such evaporation. This may be carried out by means of a technique known as "Axisymmetric Drop Shape Analysis" (ADSA) described in a publication entitled "Axisymmetric Drop Shape Analysis as a Film Balance", Colloids and Surfaces A: Physicochemical and Engineering Aspects 88(1994) 51–58 and references identified therein. This technique involves taking measurements at several coordinate points selected along the pendant drop's profile at successive time intervals and processing those measurements with a computer program designed to yield indications of surface tension and pendant drop volume.

Figure 6:
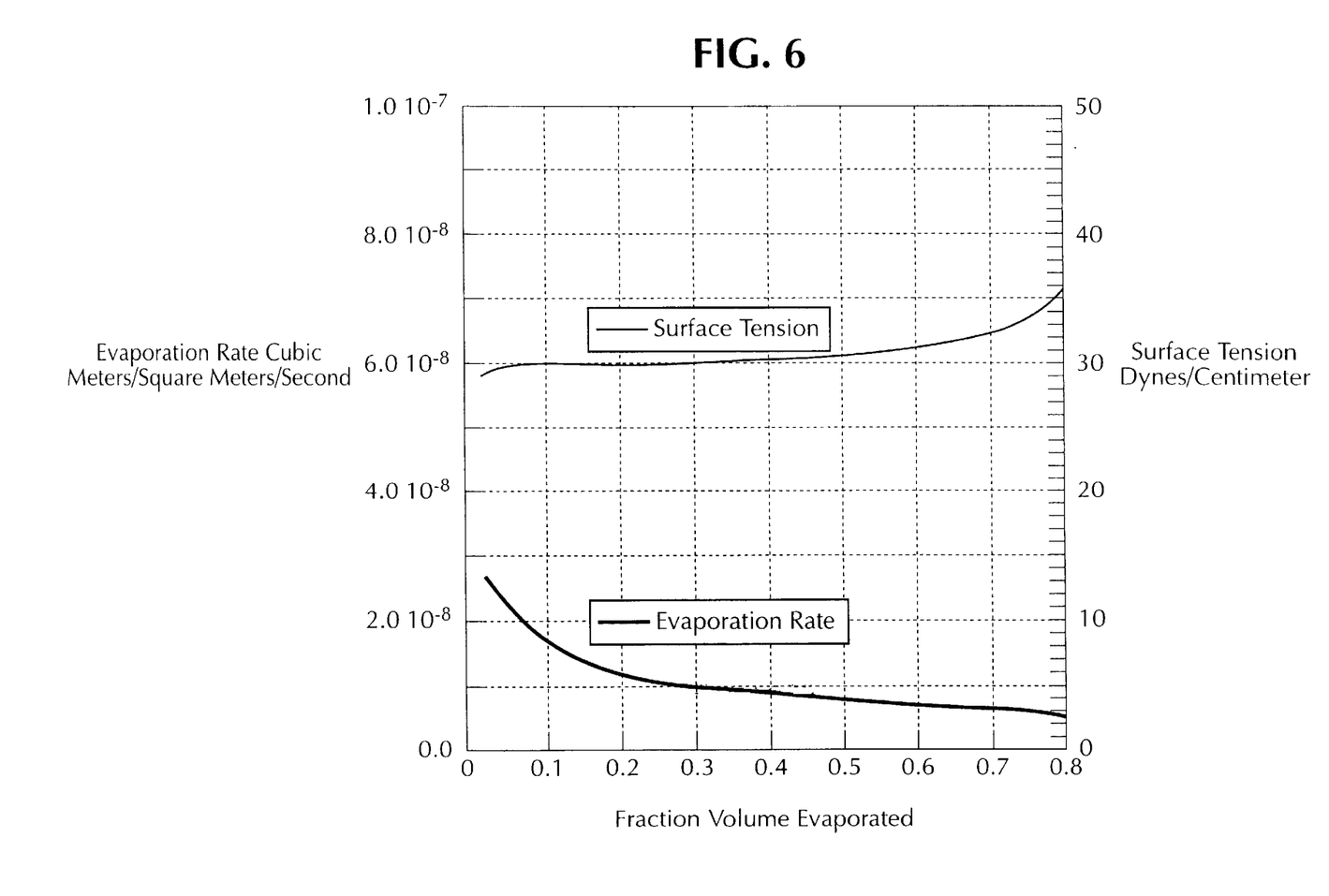
FIG. 6 is a graph showing evaporation rate of liquids from a pendant drop of a liquid under consideration, as well as the surface tension of the liquid at different fractions of volume evaporated from the pendant drop for a liquid which is not suitable for atomization and complete evaporation.
Figure 7:
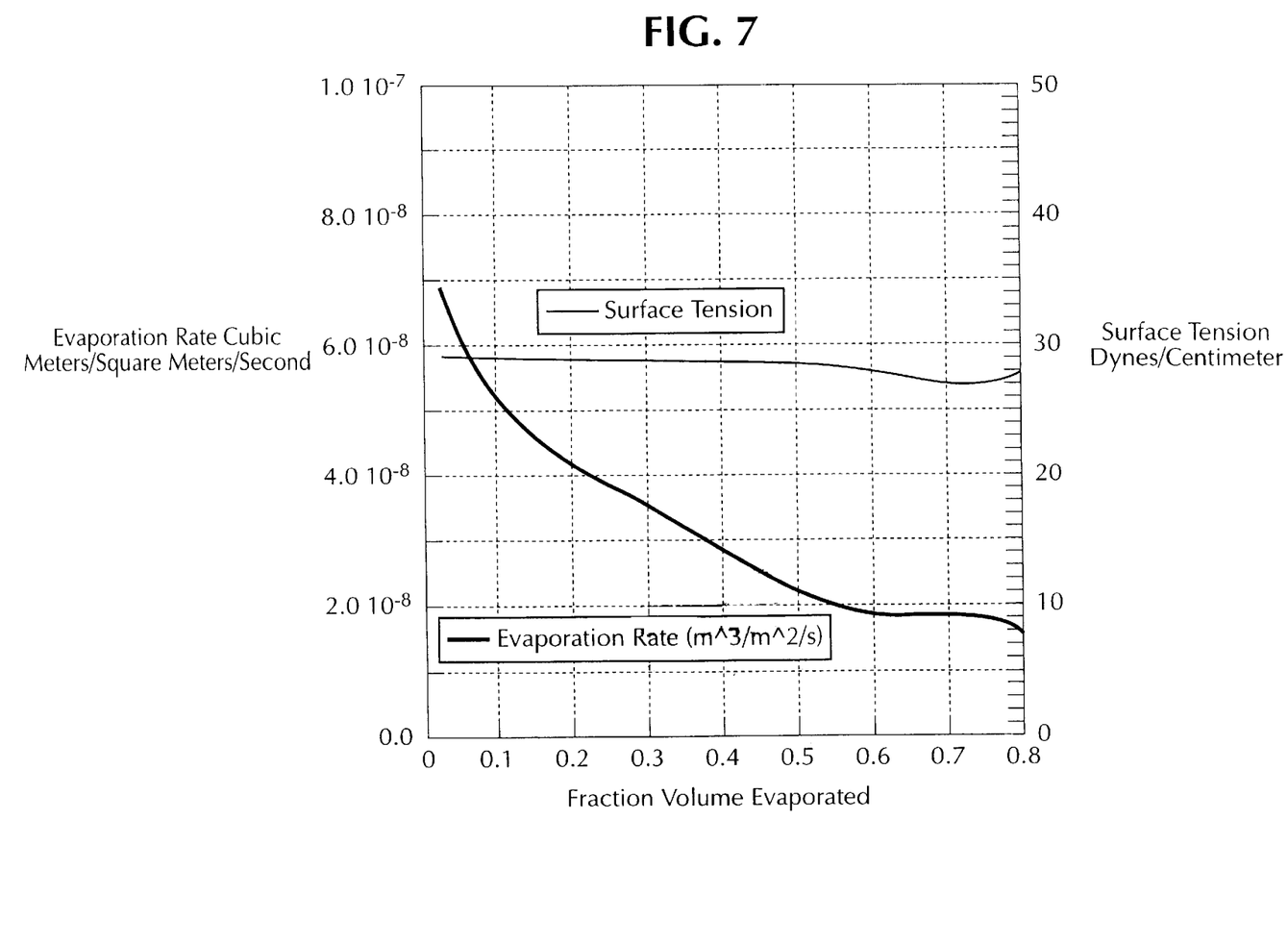
FIGS. 7 and 8 are graphs similar to those of FIG. 6, for liquids which are suitable for atomization and complete vaporization.
Figure 8:
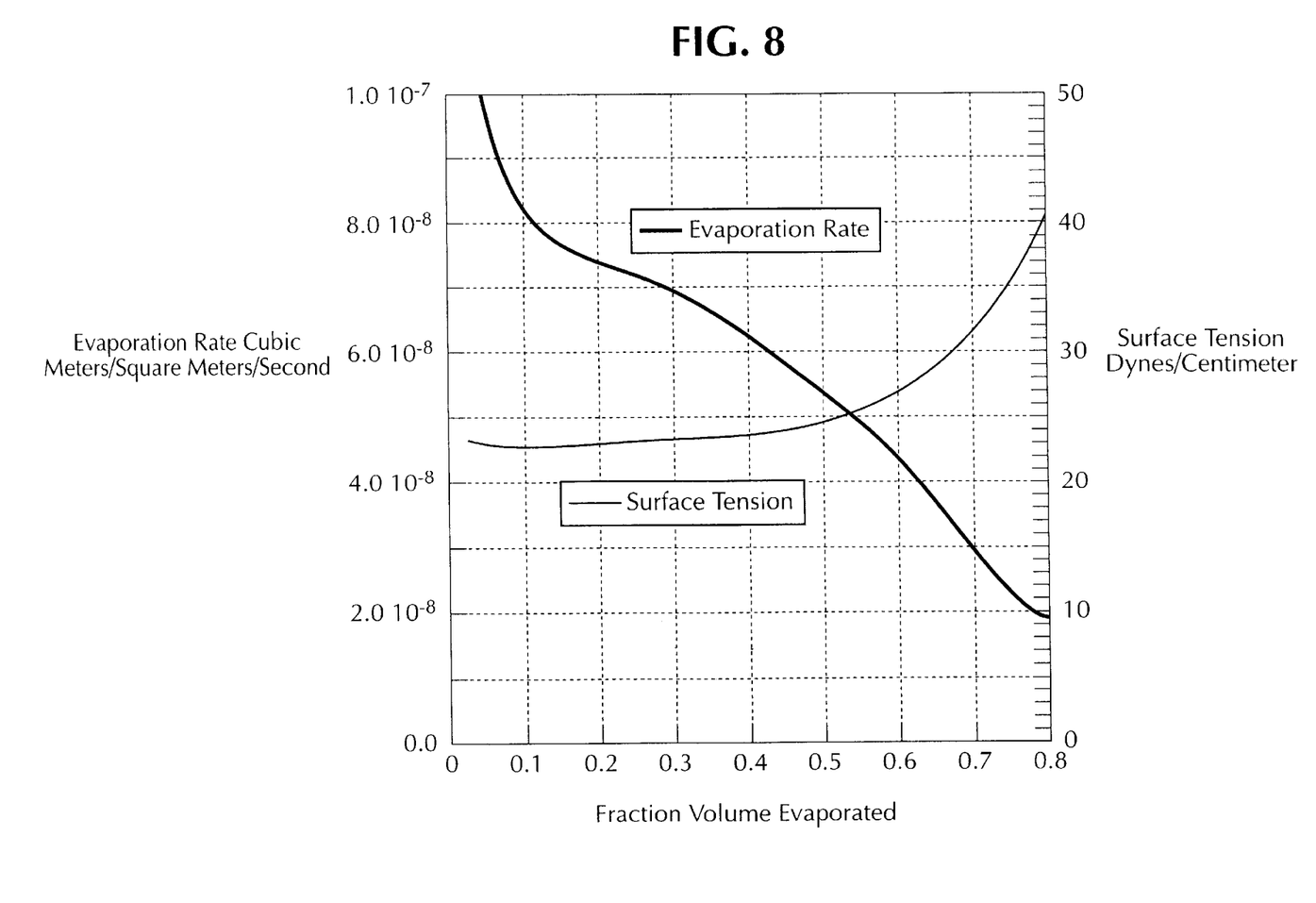

FIGS. 6, 7 and 8 are graphs showing the results of pendant drop size (evaporation rate) and droplet profile (surface tension) measurements which were made for different liquids as different portions of the test drops 54 of each liquid were measured while those pendant drops were exposed to the atmosphere. FIG. 6 shows the evaporation rate and surface tension of a pendant test drop 54 of a liquid which is unsuitable for atomization and evaporation. As can be seen in FIG. 6, the evaporation rate during the interval in which about 70 to 75% of the pendant drop 54 has evaporated is about $0.5 \times 10^{-8}$ cubic meters per square meter per second. Also the observed drop surface tension in this interval is 32–35 dynes per centimeter.

FIG. 7 shows the evaporation rate and surface tension of a drop 54 of a liquid which is suitable for atomization in a vibrating plate atomizer and ejection of droplets as large as 50 microns to a height of at least 8 centimeters above an adjacent surface. Such droplets will completely evaporate before reaching the adjacent surface. As can be seen in FIG. 7, the evaporation rate during the interval in which 70 to 75% of the pendant drop 54 has evaporated is about 1.6 to $1.8 \times 10^{-8}$ cubic meters per square meter per second. Also, the observed drop surface tension in this interval is 24–26 dynes per centimeter.

FIG. 8 shows the evaporation rate and surface tension of a pendant test drop 54 of another liquid which is suitable for atomization in a vibrating plate atomizer and ejection of droplets as large as 50 microns to a height of at least 8 centimeters above an adjacent surface. As can be seen in FIG. 8, the evaporation rate during the interval in which about 70% of the pendant test drop 54 has evaporated is about 2.0 to $3.0 \times 10^{-8}$ cubic meters per square meter per second. Also the observed droplet surface tension in this interval is about 34 dynes per centimeter.

It will be appreciated that by providing a pendant drop evaporation test as described herein in which the evaporation rate and surface tension of a droplet of a liquid in question is ascertained, it is possible to determine whether the liquid would be suitable for complete evaporation using a vibrating plate type atomizer. Moreover, by means of this technique there is no need to measure or to even know the vapor pressures of the individual components of the liquid. Thus, with this invention multi-component liquids having large numbers of different liquid components can easily be analyzed for evaporability in a vibrating plate type atomizer.

INDUSTRIAL APPLICABILITY

The present invention makes it possible to assure complete evaporation from atomized droplets of fragrances or insecticides having given diameters when they are ejected to predetermined heights above a surface toward which they fall after ejection. In this manner the surface is protected from chemical attack or other deleterious effects of the liquid fragrance or insecticide.

What is claimed is:

1. A method of evaporating a multi-component liquid solution comprising the steps of:

using a vibrating plate atomizer to form a mist or cloud of small liquid droplets of the solution;

ejecting said mist or cloud of small droplets into the atmosphere; and allowing said droplets to fall back toward an adjacent surface;

said liquid solution comprising a plurality of components having respective vapor pressures, the component having substantially the lowest vapor pressure being related to those droplets having the larger diameters such that $$1.2\times10^{12}\times D_p^4/[H\times P_v]\leq 1$$

where $D_p$ is the diameter, in centimeters, of the larger diameter droplets, H is substantially the height, in centimeters, to which said larger diameter droplets are ejected, and $P_v$ is the vapor pressure, in millimeters of Hg of the component having substantially the lowest vapor pressure;

whereby the amount of unevaporated liquid that falls back upon said adjacent surface is minimized.

2. A method according to claim 1, wherein said multi-component liquid comprises a multi-component liquid fragrance or a multi-component liquid insecticide.

3. A method according to claim 2, wherein, the values of $D_p$, H and $P_v$ are chosen in conjunction with the effects of said liquid on said adjacent surface such that any unevaporated liquid that does fall back onto said surface is in an amount insufficient to cause an adverse effect on said surface.

4. A method according to claim 2, wherein, said component having the lowest vapor pressure constitute less than about 2% of the total volume of said mist.

5. A method according to claim 2, wherein said droplets having the larger diameters constitute less than about 10% of the total liquid volume of said mist.

6. A method according to claim 2, wherein said height is in the range of 5 to 20 centimeters above said surface.

7. A method according to claim 2, wherein said larger diameter droplets have diameters greater than about 10 microns.

8. A method according to claim 2, wherein the vapor pressure of the component having substantially the lowest vapor pressure is greater than about 0.008 mm Hg.

9. A method according to claim 6, wherein no more than 10% of the total liquid volume of said mist comprises droplets whose diameters are greater than 15 microns.

10. A method according to claim 6, wherein the vapor pressure of the component having substantially the lowest vapor pressure is greater than about 0.008 mm Hg.

11. A method according to claim 7, wherein said height is in the range of 5 to 20 centimeters above said surface.

12. A method according to claim 7, wherein the vapor pressure of the component having substantially the lowest vapor pressure is greater than about 0.008 mm Hg.

13. A method according to claim 2, wherein the larger diameter droplets have diameters greater than about 15 microns and constitute less than about 10% of the total liquid volume of said mist, and wherein the vapor pressure of the component having substantially the lowest vapor pressure is greater than about 0.008 mm Hg.

14. A method according to claim 13, wherein said height is in the range of 5 to 20 centimeters above said surface.

15. A method according to claim 2, wherein the vapor pressure of the component having substantially the lowest vapor pressure is greater than about 0.008 mm Hg, wherein said larger diameter droplets have diameters greater than about 15 microns and constitute less than about 10% of the total volume of said mist, and wherein said height is in the range of 5 to 20 centimeters.

16. Apparatus for evaporating a multi-component liquid solution, said apparatus comprising:

a liquid reservoir containing a multi-component liquid;

a liquid delivery system; and an atomizer;

said liquid delivery system being arranged to convey liquid from said reservoir to said atomizer;

said atomizer being constructed to form a mist or cloud of small liquid droplets having diameters within a predetermined range and to eject said droplets into the atmosphere to predetermined heights above an adjacent surface toward which they fall;

said multi-component liquid comprising a plurality of components having respective vapor pressures, the component having substantially the lowest vapor pressure being related to those droplets having the larger diameter such that $$1.2\times10^{12}\times D_p^4/[H\times P_v]\leq 1$$

where $D_p$ is the diameter, in centimeters, of the droplet having the largest diameter, H is the height in centimeters, to which said larger diameter droplets are ejected and $P_v$ is the vapor pressure, in millimeters of Hg, of the component having substantially the lowest vapor pressure.

17. Apparatus according to claim 16, wherein said multi-component liquid comprises a multi-component liquid fragrance or a multi-component liquid insecticide.

18. Apparatus according to claim 17, wherein, the values of $D_p$, H and $P_v$ are chosen in conjunction with the effects of said liquid on said adjacent surface such that any unevaporated liquid that does fall back onto said surface is in an amount insufficient to cause an adverse effect on said surface.

19. Apparatus according to claim 17, wherein said droplets having the larger diameters constitute less than about 10% of the total liquid volume of said mist.

20. Apparatus according to claim 17, wherein said height is in the range of 5 to 20 centimeters above said surface.

21. Apparatus according to claim 19, wherein said larger diameter droplets have diameters greater than about 10 microns.

22. Apparatus according to claim 17, wherein the vapor pressure of the component having substantially the lowest vapor pressure is greater than about 0.008 mm Hg.

23. Apparatus according to claim 20, wherein said larger diameter droplets have diameters greater than about 10 microns.

24. Apparatus according to claim 20, wherein the vapor pressure of the component having substantially the lowest vapor pressure is greater than about 0.008 mm Hg.

25. A method of evaluating a liquid for suitability for atomization by means of a vibrating plate atomizer and by evaporation of droplets produced from said atomizer, said method comprising the steps of:

forming a pendant drop of said liquid;

allowing said pendant drop to evaporate while sensing its rate of decrease in size; and producing a signal which represents suitability for atomization when said sensing indicates that said rate of decrease in size is greater than a predetermined rate.

26. A method according to claim 25, wherein said liquid is a multi-component liquid fragrance or a multi-component liquid insecticide.

27. A method according to claim 26, wherein the size of said pendant drop is about 6 microliters and said pendant drop is allowed to decrease in size by about 70% of its original volume before sensing its rate of decrease in size.

28. A method according to claim 27, wherein said liquid is to be atomized into droplets having a particle size of up to about 50 microns and ejected into the atmosphere to a height of at least 8 centimeters above a surface, and wherein said rate of decrease in size is at least $1.0 \times 10^{-8}$ cubic meters per square meter per second.

29. A method according to claim 28, wherein no more than 10% of the atomized liquid comprises droplets having diameters greater than 10 microns.

30. A method according to claim 26 and further including the steps of sensing surface tension of said drop and of limiting said signal which represents suitability for atomization to conditions where said surface tension is less than a predetermined value.

31. A method according to claim 30, wherein said liquid is to be atomized into droplets having a particle size of up to 50 microns and ejected into the atmosphere to a height of at least 8 centimeters above a surface, and wherein said value of surface tension is less than 35 dynes per centimeter.

32. A method of ascertaining whether a multi-component liquid fragrance or a multi-component liquid insecticide, when atomized into droplets having a particle size of up to 50 microns and ejected into the atmosphere to a height of at least 8 centimeters above a surface, and where no more than 10% of the total volume of the droplets is larger than 15 microns, will be suitable for complete evaporation before falling back onto the surface, said method comprising the steps of:

forming a pendant drop of said liquid, the size of said pendant drop being about 6 microliters;

allowing said pendant drop to evaporate while sensing its size;

when the pendant drop has become reduced in size by about 70% of its original volume, calculating its rate of evaporation and its surface tension; and providing an indication of suitability for complete evaporation when the evaporation rate of said pendant drop is at least $1.0 \times 10^{-8}$ cubic meters per square meter per second and the surface tension of said droplet is no more than 35 dynes per centimeter.

33. Apparatus for evaluating a liquid for suitability for atomization by means of a vibrating plate atomizer and by evaporation of droplets produced from said atomizer, said apparatus comprising:

means for forming a pendant drop of said liquid and suspending said drop while liquid evaporates therefrom;

a sensor constructed and arranged to sense a rate of decrease in size of the pendant drop during evaporation of liquids therefrom; and an indication producing device connected to said sensor and to produce a signal which represents suitability for atomization when said sensor indicates that said rate of decrease in size is greater than a predetermined rate.

34. Apparatus according to claim 33, wherein said liquid is a multi-component liquid fragrance or a multi-component liquid insecticide, wherein said pendant drop is initially 6 microliters, and wherein said sensor senses said rate of decrease in size when said pendant drop has decreased in size by about 70% of its original volume.

35. Apparatus according to claim 34, wherein said sensor and said indication producing device are programmed to produce an indication of suitability of the liquid for atomization where said liquid is to be atomized into droplets having a particle size of up to 50 microns and ejected into the atmosphere to a height of at least 8 centimeters above a surface, and wherein said rate of decrease in size is at least $1.0 \times 10^{-8}$ cubic meters per square meter per second.

36. Apparatus according to claim 35, wherein said sensor is constructed to sense surface tension of said drop and to limit said signal which represents suitability for atomization to conditions where said surface tension is less than a predetermined value.

37. Apparatus according to claim 36, wherein said sensor and said indication producing device are programmed to provide an indication of suitability of said liquid for evaporation in a vibrating plate atomizer which atomizes said liquid into droplets having a particle size of up to 50 microns, with no more than 10% of the total volume of said droplets comprising droplets larger than 15 microns, wherein said droplets are ejected into the atmosphere to a height of at least 8 centimeters above a surface, and wherein said surface tension is less than 35 dynes per centimeter.

38. Apparatus for ascertaining whether a multi-component liquid fragrance or a multi-component liquid insecticide, when atomized into droplets having a particle size of up to 50 microns and ejected into the atmosphere to a height of at least 8 centimeters above a surface, will be suitable for complete evaporation before falling back onto the surface, said apparatus comprising:

a drop forming means which forms a pendant drop of said liquid about 6 microliter in size and allows said droplet to evaporate;

a sensor constructed and arranged to sense a rate of decrease in size of the pendant drop during evaporation of liquids therefrom; and an indication producing device connected to said sensor and to produce a signal which represents suitability for atomization when said sensor indicates that said rate of decrease in size of the pendant drop is greater than a predetermined rate;

said sensor and said indication means being arranged such that when the pendant drop has become reduced in size by about 70% of its original volume, its rate of evaporation and its surface tension are sensed and an indication of suitability for complete evaporation is provided when the evaporation rate of said pendant drop is at least $1.0 \times 10^{-8}$ cubic meters per square meter per second and the surface tension of said pendant drop is no more than 35 dynes per centimeter.

39. A method of evaporating a multi-component liquid solution, said method comprising the steps of:

operating a vibrating plate atomizer to form a mist or cloud of small liquid droplets of the solution;

ejecting said mist or cloud of small droplets into the atmosphere; and allowing said droplets to fall back toward an adjacent surface, said liquid solution having evaporation characteristics such that the size of a pendant drop of the liquid decreases at a predetermined rate which corresponds to evaporation of said liquid droplets prior to falling on an adjacent surface after having been ejected into the atmosphere by said atomizer, said evaporation being such that the unevaporated liquid in said droplets is insufficient to have an adverse effect on said surface.

40. A method according to claim 39, wherein said multi-component liquid solution is a multi-component liquid fragrance or a multi-component liquid insecticide.

41. A method according to claim 40, wherein no more than 10% of the total liquid volume of said mist or cloud comprises droplets whose diameter is greater than 15 microns.

42. A method according to claim 41, wherein said pendant drop is approximately 6 microns and wherein the size of said drop decreases at a rate of at least $1.0 \times 10^{-8}$ cubic meters per square meters per second after approximately 70% of the original volume of said pendant drop has evaporated.

\* \* \* \* \*